US008031342B2

(12) United States Patent
Goossen

(10) Patent No.: US 8,031,342 B2
(45) Date of Patent: Oct. 4, 2011

(54) SENSOR AND SENSING UTILIZING A LASER

(75) Inventor: Keith Goossen, Howell, NJ (US)

(73) Assignee: Empire Technology Development LLC, Wilmington, DE (US)

( * ) Notice: Subject to any disclaimer, the term of this patent is extended or adjusted under 35 U.S.C. 154(b) by 324 days.

(21) Appl. No.: 12/401,380

(22) Filed: Mar. 10, 2009

(65) Prior Publication Data
US 2010/0231916 A1 Sep. 16, 2010

(51) Int. Cl.
*G01N 21/55* (2006.01)
(52) U.S. Cl. ................ 356/448; 356/445
(58) Field of Classification Search ........... 356/445–448
See application file for complete search history.

(56) References Cited

U.S. PATENT DOCUMENTS

| | | | | |
|---|---|---|---|---|
| 5,793,485 | A | * | 8/1998 | Gourley ............ 356/318 |
| 5,812,272 | A | * | 9/1998 | King et al. ............ 506/39 |
| 7,190,851 | B2 | | 3/2007 | Grace et al. ............ 385/12 |
| 7,268,864 | B2 | * | 9/2007 | Chiarello et al. ........ 356/128 |
| 7,354,772 | B2 | * | 4/2008 | Menon et al. ............ 436/164 |
| 2006/0077382 | A1 | * | 4/2006 | Wang et al. ............ 356/301 |
| 2008/0230716 | A1 | * | 9/2008 | Tysoe et al. ............ 250/459.1 |
| 2008/0240543 | A1 | * | 10/2008 | Budach et al. ............ 382/141 |
| 2009/0040597 | A1 | * | 2/2009 | Rae et al. ............ 359/330 |
| 2010/0328671 | A1 | * | 12/2010 | Baldo et al. ............ 356/445 |

OTHER PUBLICATIONS

K. W. Goossen et al.; "GaAs nm Modulators Solder-Bonded to Silicon"; IEEE Photonics Technology Letters, vol. 5, No. 7, Jul. 1993, pp. 776-778.
A. V. Krishnamoorthy et al. "3-D Integration of MQW Modulators Over Active Submicron CMOS Circuits: 375 Mb/s Transimpedance Receiver-Transmitter Circuit"; IEEE Photonics Technology Letters, vol. 7, No. 11, Nov. 1995, pp. 1288-1290.
A. L. Lentine et al.; "Arrays of Optoelectronic Switching Nodes Comprised of Flip-Chip-Bonded MQW Modulators and Detectors on Silicon CMOS Circuitry"; IEEE Photonics Technology Letters, vol. 8, No. 2, Feb. 1996, pp. 221-223.
A. V. Krishnamoorthy et al.; "16×16 VCSEL Array Flip-Chip Bonded to CMOS VLSI Circuit"; IEEE Photonics Technology Letters, vol. 12, No. 8, Aug. 2000, pp. 1073-1075.

* cited by examiner

*Primary Examiner* — Tarifur R Chowdhury
*Assistant Examiner* — Michael LaPage
(74) *Attorney, Agent, or Firm* — Dorsey & Whitney LLP

(57) ABSTRACT

Embodiments are generally described that include lasers having two mirrors, at least one of which has a reflectivity related to a presence or concentration of a target analyte. Output radiation generated by the laser may be related to the presence of the target analyte.

19 Claims, 3 Drawing Sheets

SENSOR AND SENSING UTILIZING A LASER

BACKGROUND

Chemical and biological sensors may be used to sense the presence of a particular chemical or biological agent. It may be difficult to integrate sensing capability for chemical or biological agents with sensing electronics and other supporting systems.

Optical sensors for chemical and biological agents have utilized a material whose optical properties change in the presence of the chemical or biological agent. A light source is used to illuminate the material through a transmission path such as an optical fiber or other waveguide. A change in the transmission of light through the material when the chemical or biological agent is present may be used to detect the agent. Such a system may be bulky, cumbersome and expensive due to the need to provide a length of material through which the light can be transmitted, and the optical path between the light source and the material.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

DETAILED DESCRIPTION

Figure 1:
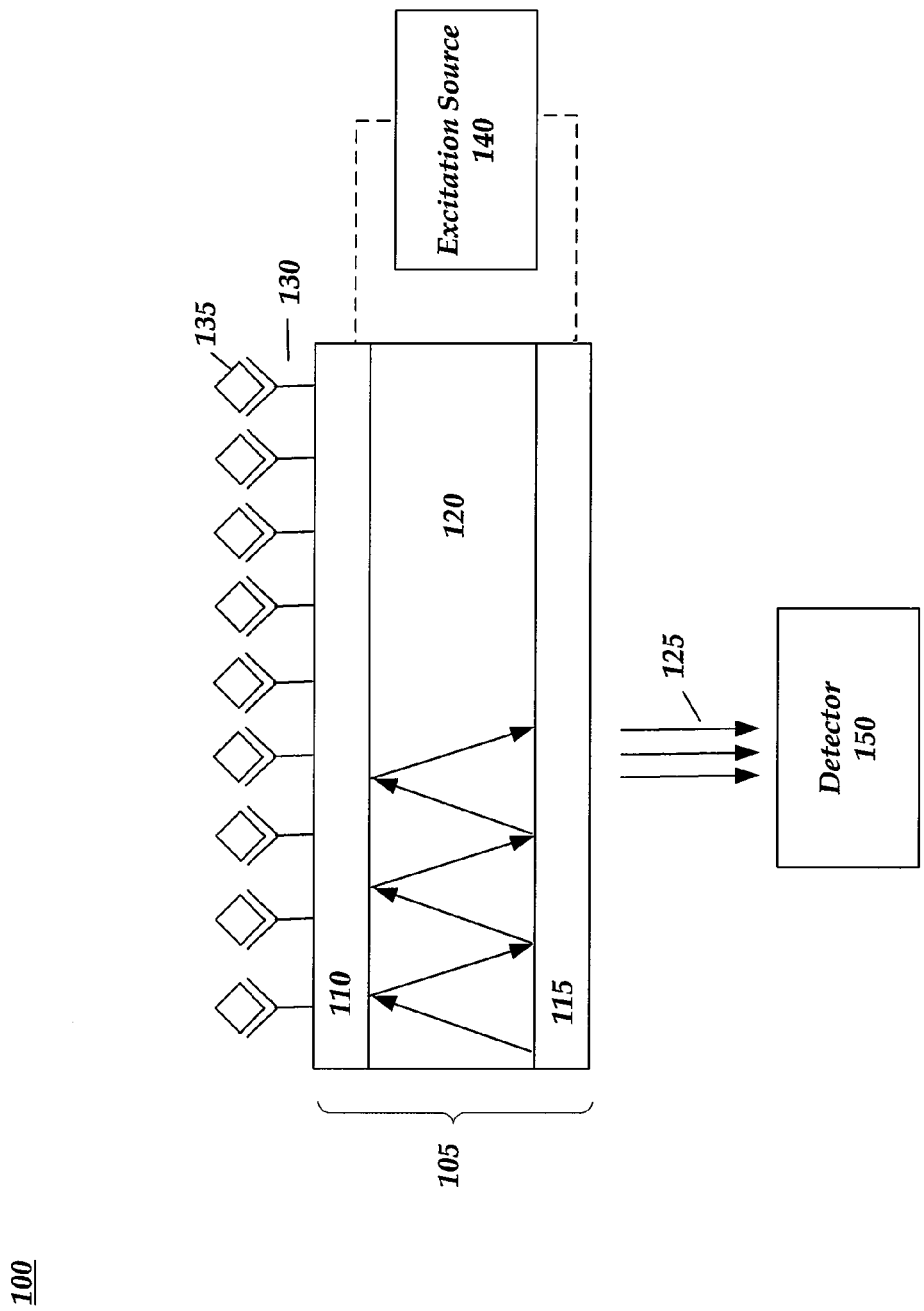
FIG. 1 is a schematic illustration of an example sensor utilizing a laser.

The following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

Certain details are set forth below to provide a sufficient understanding of embodiments of the present disclosure. However, it will be clear to one skilled in the art that embodiments of the invention may be practiced without various of these particular details. In some instances, well-known electrical components, circuits, control signals, software operations, analytes, materials, and fabrication techniques have not been shown in detail in order to avoid unnecessarily obscuring the described embodiments of the invention.

FIG. 1 is a schematic illustration of an example sensor 100 utilizing a laser 105 arranged in accordance with at least some embodiments of the present disclosure. The laser 105 includes two mirrors 110 and 115, which also may be referred to as facets, and a gain medium 120. The mirrors 110 and 115 and the gain medium 120 may be implemented using any suitable materials for forming lasers. As generally understood in the art, when stimulated by an excitation source 140, optical energy is amplified within the gain medium 120 as it is reflected between the reflective surfaces 110 and 115, as generally shown in FIG. 1. The laser 105 accordingly produces output radiation 125. Generally, any type of laser may be used, including but not limited to a ruby laser, a vertical-cavity surface-emitting laser (VCSEL), a laser diode, or combinations thereof.

Embodiments of the present disclosure include lasers whose output is related to the presence of a target analyte. Accordingly, embodiments of sensors according to the present disclosure include lasers having one or more mirrors whose reflectivity properties change in the presence of a target analyte. Embodiments of mirrors useful with embodiments of the present disclosure include those formed from materials that are themselves sensitive to the presence of a target analyte, and those having a coating or other sensitive layer applied to at least one surface. For example, as shown in FIG. 1, antibodies 130 are provided on a surface of the mirror 110. The antibodies 130 may bind to a target analyte 135. Once the target analyte 135 is bound to the antibody 130, the presence of the target analyte 135 may alter the reflection of the optical energy within the gain medium 120. Without being bound by theory, the presence of the target analyte 135 may absorb or reflect energy at or around the lasing wavelength, altering the reflection of optical energy within the gain medium 120. Accordingly, the radiation output 125 of the laser may change in the presence of the target analyte.

Although shown coupled directly to the surface of the mirror 110 in FIG. 1, the antibodies 130 may be coupled to the mirror 110 by an adhesion or other material layer in some embodiments. Further, in some embodiments, an antibody or other material attachment to the mirror 110 may not be required, the mirror 110 could itself be implemented of a material whose optical properties are sensitive to the presence of a target analyte. In some embodiments, rather than the antibodies 130, other coatings or binding ligands may be applied or coupled to a surface of the mirror 110. The choice of particular mirror material, mirror coating, enzyme, binding ligand, antibody, or combinations thereof, used to implement embodiments of the present disclosure will vary according to the particular laser used, and materials used to form the laser, as well as the particular target analyte to be sensed. Examples of coatings usable with embodiments of the present disclosure include cyclodextrin derivatives and calixarenes that may form inclusion complexes with target analytes, as described in U.S. Pat. No. 7,190,851, which patent is hereby incorporated by reference in its entirety for any purpose.

Sensors according to embodiments of the present disclosure may respond to any of a variety of target analytes. Target analytes may accordingly include any chemical or biological compound of interest including chemicals, toxins, proteins, DNA or RNA molecules, gasses, liquids, or combinations thereof.

In operation, the excitation source 140 may be coupled to the laser 105 to initiate the reflection within the gain medium 120 and produce the output radiation 125. The excitation source 140 may be any suitable source for the laser used. Excitation sources usable with embodiments of the present disclosure include radiation sources, voltage sources, current sources, or combinations thereof. For example, in the embodiment shown in FIG. 1 the excitation source 140 may be coupled to the mirrors 110 and 115. The laser 105 may be implemented as a diode where one of the mirrors 110 and 115 is made of a p-type material and the other of an n-type material. The excitation source 140 may include a voltage source to forward bias the diode, and initiate internal reflections in the gain medium 120.

Output radiation 125 may be detected by a detector 150. The detector 150 may be implemented by any type of detector suitable for detecting the output radiation 125, including a photodiode or other photo-sensitive electronics. As generally described above, the presence of the target analyte 135 may alter the output radiation 125 of the laser 105. Accordingly, the presence of the target analyte 135 may be detected by monitoring the output radiation 125 for a change indicative of the presence of the target analyte 135, such as an increase or decrease in output power of the laser 105. In some embodiments, the mirror 115 closest to the detector 150 is fabricated or treated to have a lower reflectance than the mirror 110 so that more light is received by the detector 150. In other embodiments, however, continuous monitoring may not be necessary. In some embodiments one or more threshold values of laser output power may be stored, for example in a memory (not shown). The excitation source 140, detector 150, and combinations thereof, may not operate continuously, but may monitor at periodic or other intervals the output radiation 125 of the laser 105 and compare the output radiation 125 to a level known to be indicative of a target analyte, or of the lack of a target analyte in order to determine the presence of the target analyte. In some embodiments, the presence of the target analyte may be detected by comparing the output radiation 125 of the laser 105 sensitive to the presence of the target analyte with output radiation of a second laser that is not sensitive to the presence of the target analyte. That is, a calibration laser may be provided without the antibody coating 130, and the output of the calibration laser compared with the output radiation 125 to determine the presence of the target analyte. In still other embodiments, a laser output may be calibrated such that a concentration of target analyte could be determined based on the output radiation of the laser. Output radiation levels corresponding to different target analyte concentrations may be stored in a memory, or the output radiation of a sensor may be compared with a calibration sensor having a known concentration of target analyte present.

Figure 2:
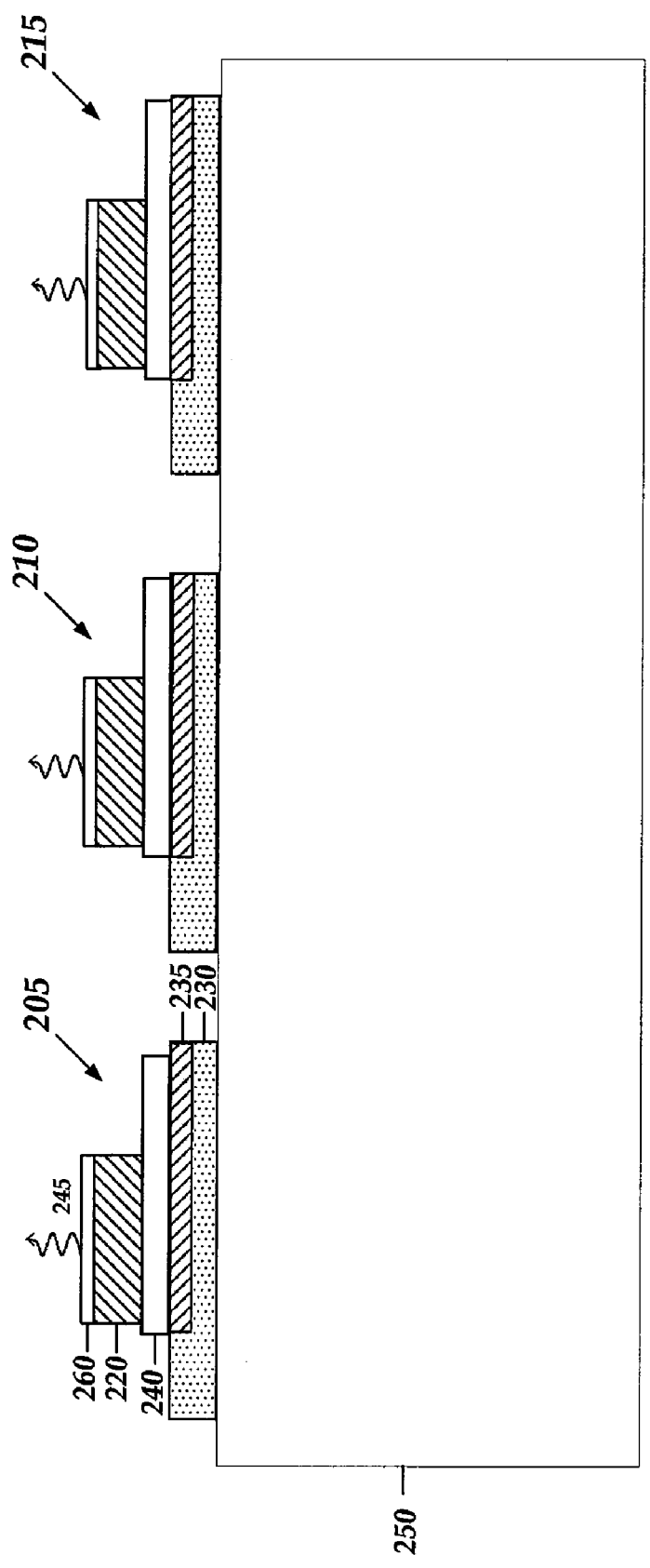
FIG. 2 is a schematic illustration of three vertical-cavity surface-emitting lasers (VCSELs) that may be used to form integrated sensors.

In some embodiments, all or portions of the excitation source 140, detector 150, or both, may be integrated with the laser 105. FIG. 2 is a schematic illustration of three vertical-cavity surface-emitting lasers (VCSELs) 205, 210, and 215 that may be used to form integrated sensors, in accordance with at least some embodiments of the present disclosure. The VCSEL structures for implementing the lasers 205, 210 and 215 are not limited to the example structures described herein, and other reasonable substitutions are also contemplated.

Briefly, each VCSEL includes two mirrors and gain medium between a p-n diode. For example, the VCSEL 205 includes a mirror 220, a p-type contact material 240, a gain medium 235, and an n-type mirror 230. When the p-n junction formed by the material 240 and the mirror 230 is forward-biased, optical energy is reflected within the gain medium, and output radiation 245 is produced. An antibody coating 260 is coupled to the mirror 220, as described above. The antibody coating 260 may be coupled to all or a portion of the surface of the mirror 220. The presence of the antibody coating 260 may allow binding of a target analyte to the mirror 220 resulting in an amount of output radiation 245 that is based on the presence or amount of the target analyte. While the mirror 220 and the p-type contact material 240 are shown as separate materials in FIG. 2, in other embodiments a single material may form both the mirror 220 and the contact material 240. Further, although the n-type mirror 230 is shown on the bottom of the material stack in FIG. 2, in some embodiments, the n-type mirror 230 may be at the top. VCSELs such as the VCSELs 205, 210, and 215 may be formed using semiconductor manufacturing processes on a substrate 250. The substrate may be, for example, gallium arsenide, GaAs. Although three VCSELs 210, 215, and 220 are shown on the substrate 250 in FIG. 2, generally any number may be fabricated on the substrate, and an array of VCSELs may also be fabricated.

Figure 3:
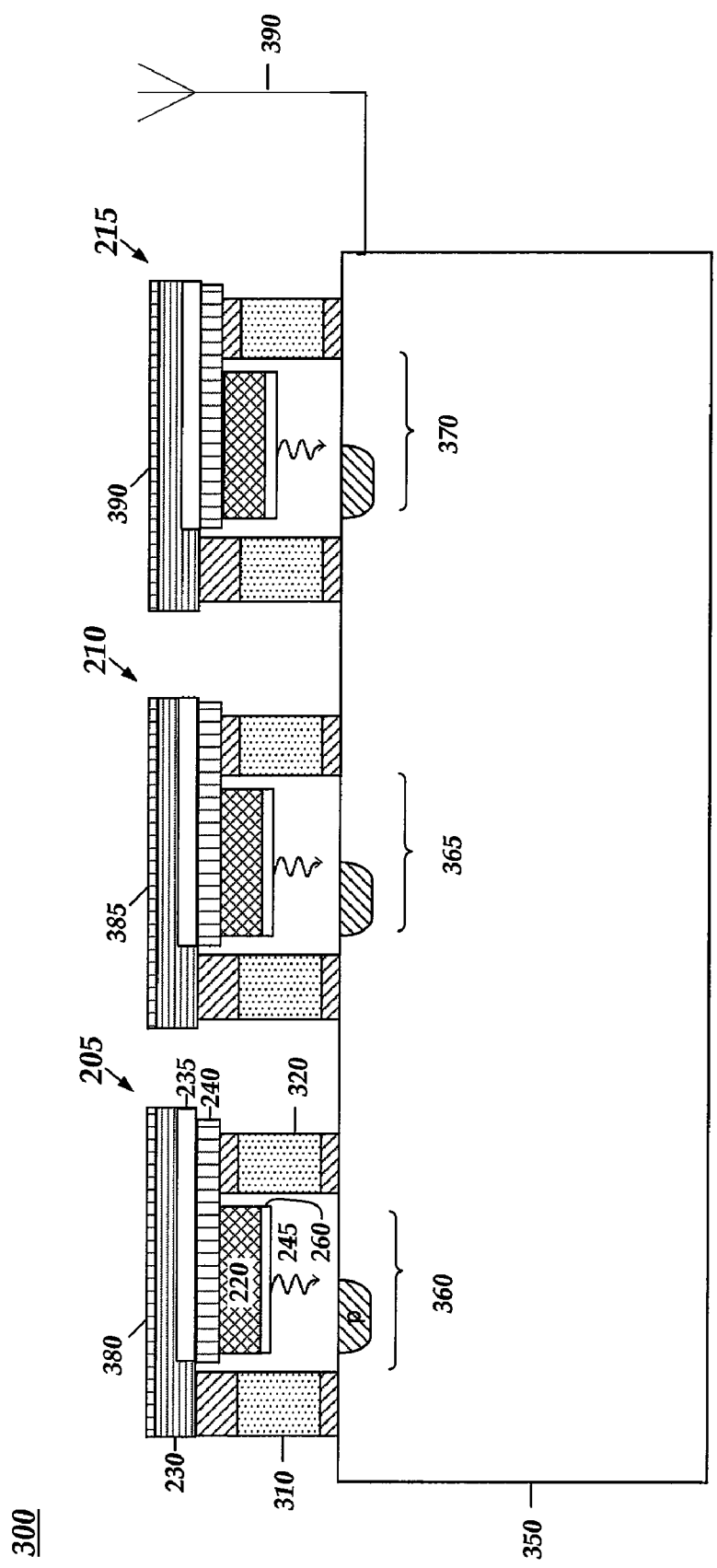
FIG. 3 is a schematic illustration of another example sensor utilizing the three VCSELs of FIG. 2, all arranged in accordance with at least some embodiments of the present disclosure.

FIG. 3 is a schematic illustration of an example sensor 300 utilizing the three VCSELs 205, 210, and 215 of FIG. 2, arranged in accordance with at least some embodiments of the present disclosure. The VCSELs 205, 210, and 215 may be integrated with drive electronics used to forward-bias the p-n junction of one or more of the VCSELs 205, 210, and 215. For example, the VCSELs 205, 210, and 215 may be flip-chip bonded onto a substrate 350 as shown in FIG. 3. The substrate 350 may be any suitable substrate, including but not limited to a silicon substrate. The flip-chip bumps, such as the bumps 310 and 320 are conductive couplings, such as solder bumps, that may make electrical contact to drive electronics (not shown) on the substrate 350. For example, the bump 310 may make electrical contact between the p-type contact material 240 and drive electronics, while the bump 320 may make electrical contact between the n-type mirror 230 and the drive electronics. The drive electronics may be used to forward bias the p-n junction, and drive one or more of the VCSELs 205, 210, and 215. Photodiodes 360, 365, and 370 may be formed in the substrate 350 to detect output radiation from the VCSELs 205, 210, and 215, respectively. The photodiodes 360, 365, and 370 each include a p-n junction in the substrate 350 whose properties may change in the presence of output radiation from the respective VCSEL. In this manner, drive electronics and detectors may be integrated with one or more lasers.

The substrate 250 has been removed from the n-type mirror 230 in FIG. 3. To form the sensor 300, sensing layers 380, 385, and 390 are provided on each of the n-type mirrors of the respective VCSELs 205, 210 and 215. The sensing layers 380, 385, and 390 may be sensitive to the same or to different target analytes. Although shown with a thickness in FIG. 3, the sensing layers 380, 385, and 390 (along with the rest of the Figure) are not drawn to scale. In some embodiments, the sensing layers 380, 385, and 390 may be as thin as a monolayer of material. In this manner, each of the VCSELs 205, 210, and 215 may operate to detect a different target analyte. Accordingly, any number of target analytes may be detected using a sensor 300 on a single substrate 350 based on the number of VCSELs provided. For example, each of the VCSELs 205, 210, and 215 may be coated with a different antibody.

Further, in some embodiments, as generally described above, one or more of the VCSELs in the sensor 300 may be used as a calibration sensor and may not be sensitive to the presence of a particular target analyte. In this manner, output radiation from the calibration sensor and another of the VCSELs may be compared to determine a presence of the target analyte.

Sensors according to embodiments of the present disclosure may find use in a variety of applications, including but not limited to security applications for sensing the presence of a chemical or biological agent present in the atmosphere. Sensors, such as the sensor 300 in FIG. 3, may be deployed in locations such as but not limited to buildings, residences, stadiums, public city streets, parks, subways, or other transportation vehicles. The sensors may be in communication with a computing device using wireless communication, such as through antenna 390, which in some embodiments may be integrated on the substrate 350. In some embodiments, other protocols, communication techniques, or both, may be used to report sensor readings, or may report only alarms once the presence of a target analyte had been determined. Accordingly, the computing device may receive an indication of what target analyte had been identified at what location. In this manner, centralized monitoring of a large area for chemical or biological agents may be performed.

The present disclosure is not to be limited in terms of the particular examples described in this application, which are intended as illustrations of various aspects. Many modifications and examples can may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A sensor configured to receive energy from an excitation source, the sensor comprising:
   a first mirror, the first mirror having a reflectivity related to a presence of a target analyte;
   a second mirror; and
   a gain medium between the first and second mirrors, the gain medium configured to amplify the energy received from the excitation source wherein the cooperative operation of the first mirror, the second mirror and the gain medium is arranged to generate output radiation in response to the energy received from the excitation source, the output radiation related to the presence of the target analyte; and a detector positioned to receive the output radiation transmitted through the second mirror.

2. The sensor according to claim 1 wherein the first mirror comprises a first mirror material having a first surface and a coating on the first surface, the coating suitable to bind with the target analyte.

3. The sensor according to claim 1 wherein the coating comprises an antibody.

4. The sensor according to claim 1 wherein the laser is configured to generate an amount of output radiation based in part on the presence of the target analyte.

5. The sensor according to claim 1 wherein the first mirror includes a material whose reflectivity is related to the presence of the target analyte.

6. The sensor according to claim 1 wherein the detector is configured to monitor the output radiation generated by the sensor, detect a change in the output radiation generated by the laser and indicate the presence of the target analyte based on the change.

7. The sensor according to claim 1 wherein the detector is configured to compare the output radiation with a calibration value and indicate the presence of the target analyte based in part on the comparison.

8. The sensor according to claim 1 further comprising a calibration laser, the calibration laser configured to generate calibration output radiation substantially unrelated the presence of the target analyte, the detector configured to compare the output radiation with the calibration output radiation and indicate the presence of the target analyte based in part on the comparison.

9. The sensor according to claim 1 wherein the laser comprises a vertical-cavity surface-emitting laser coupled to a substrate with at least one flip-chip bump, and wherein the excitation source and the detector are supported by the substrate.

10. The sensor according to claim 9 wherein the detector comprises a photodiode formed in the substrate.

11. A sensor system comprising:
a substrate;
an array of lasers supported by the substrate, each laser comprising:
a first mirror, the first mirror having a reflectivity related to a presence or concentration of a respective target analyte;
a second mirror; and
a gain medium between the first and second mirrors;
an excitation source coupled to at least one of the lasers of the array, the excitation source configured to excite the respective laser to generate output radiation, an amount of output radiation based in part on the presence or concentration of the respective target analyte; and
a detector coupled to at least one of the lasers, wherein the detector is configured to receive the output radiation transmitted through the second mirror and also configured to generate a detection signal based on the output radiation.

12. The sensor according to claim 11 wherein each of the lasers is sensitive to a presence of a different target analyte.

13. The sensor according to claim 11 wherein the array of lasers comprises an array of vertical-cavity surface-emitting lasers.

14. The sensor according to claim 13 wherein the first mirror of each of the respective lasers is coated with a different antibody configured to bind to the respective target analyte.

15. A method for detecting a target analyte, the method comprising:
exciting a laser to produce an amount of output radiation related to a presence or concentration of the target analyte, wherein the laser includes a gain medium between a first mirror having a reflectivity related to a presence of a target analyte and a second mirror;
detecting the amount of output radiation transmitted through the second mirror; and
indicating the presence or concentration of the target analyte based on the amount of output radiation.

16. The method according to claim 15 wherein the act of indicating the presence of the target analyte comprises comparing the amount of output radiation with a calibration amount.

17. The method according to claim 16 further comprising exciting a calibration laser to produce the calibration amount of output radiation.

18. The method according to claim 15 wherein the act of indicating the presence of the target analyte comprises transmitting the indication over a wireless communication network.

19. The method according to claim 15 wherein the method further comprises exciting a plurality of lasers to produce respective amounts of output radiation, each respective amount of output radiation related to a presence of a respective target analyte;
detecting the respective amounts of output radiation; and
indicating the presence of one or more target analytes based on the respective amount of output radiation.

* * * * *

UNITED STATES PATENT AND TRADEMARK OFFICE
CERTIFICATE OF CORRECTION

| | | Page 1 of 1 |
|---|---|---|
| PATENT NO. | : 8,031,342 B2 | |
| APPLICATION NO. | : 12/401380 | |
| DATED | : October 4, 2011 | |
| INVENTOR(S) | : Keith Goossen | |

It is certified that error appears in the above-identified patent and that said Letters Patent is hereby corrected as shown below:

| Column, Line | Reads | Should Read |
|---|---|---|
| Column 4, Line 12 | "VCSELs 210, 215, and 220" | --VCSELs 205, 210, and 215-- |
| Column 7, Line 30 | "substantially unrelated the" | --substantially unrelated to the-- |
| Column 7, Line 35 | "wherein the laser" | --wherein the sensor-- |

Signed and Sealed this
Tenth Day of January, 2012

David J. Kappos
*Director of the United States Patent and Trademark Office*